(12) United States Patent
Gassner et al.

(10) Patent No.: US 11,232,871 B1
(45) Date of Patent: Jan. 25, 2022

(54) SYSTEM AND METHOD FOR EXCHANGING CLINICAL DATA

(71) Applicant: Veeva Systems Inc., Pleasanton, CA (US)

(72) Inventors: Peter Gassner, Pleasanton, CA (US); Jon Stone, Manteca, CA (US); Stephen Paul Harper, Oakland, CA (US); Jason Methia, Tiverton, RI (US); Todd Tullis, San Francisco, CA (US); Tyler James Jensen, Dublin, CA (US); Jeremy House, Oakland, CA (US)

(73) Assignee: Veeva Systems Inc., Pleasanton, CA (US)

( * ) Notice: Subject to any disclaimer, the term of this patent is extended or adjusted under 35 U.S.C. 154(b) by 42 days.

(21) Appl. No.: 16/051,353

(22) Filed: Jul. 31, 2018

(51) Int. Cl.
*G16H 80/00* (2018.01)
*G16H 10/60* (2018.01)
*G16H 10/20* (2018.01)

(52) U.S. Cl.
CPC ............ *G16H 80/00* (2018.01); *G16H 10/20* (2018.01); *G16H 10/60* (2018.01)

(58) Field of Classification Search
CPC ......... G16H 80/00; G16H 10/60; G16H 10/20
See application file for complete search history.

(56) References Cited

U.S. PATENT DOCUMENTS

| | | | | |
|---|---|---|---|---|
| 5,884,328 A * | 3/1999 | Mosher, Jr. | ......... | G06F 11/1662 |
| 8,762,341 B1 * | 6/2014 | Mahajan | ............. | G06F 11/1448 |
| | | | | 707/640 |
| 2011/0252198 A1 * | 10/2011 | Ogasawara | ............. | G06F 3/061 |
| | | | | 711/117 |
| 2013/0097117 A1 * | 4/2013 | Lasky | ................. | G06F 11/1451 |
| | | | | 707/624 |
| 2014/0074790 A1 * | 3/2014 | Berman | .............. | G06F 11/1448 |
| | | | | 707/649 |
| 2014/0142961 A1 * | 5/2014 | Luter | ..................... | G16H 10/40 |
| | | | | 705/2 |
| 2014/0304830 A1 * | 10/2014 | Gammon | ............ | G06F 21/6218 |
| | | | | 726/27 |
| 2015/0172120 A1 * | 6/2015 | Dwarampudi | ...... | H04L 67/1097 |
| | | | | 709/221 |
| 2015/0373116 A1 * | 12/2015 | Mo | ........................ | G06F 3/0647 |
| | | | | 709/219 |
| 2017/0041296 A1 * | 2/2017 | Ford | .................... | H04L 63/0421 |
| 2017/0111322 A1 * | 4/2017 | Patidar | ................ | H04L 63/0281 |
| 2017/0351716 A1 * | 12/2017 | Higginson | ............ | G06F 16/212 |
| 2018/0144292 A1 * | 5/2018 | Mattingly | ............. | G06F 16/903 |
| 2018/0276270 A1 * | 9/2018 | Bisbee | ................ | G06F 21/6218 |

(Continued)

*Primary Examiner* — Cam Y T Truong

(57) ABSTRACT

Systems and methods for exchanging clinical data among parties involved in a clinical trial. The system comprises a clinical data exchange controller, a first repository and a second repository. Repository configuration information comprises: a connection to a target repository, scope of capacities, and a rule set. Repository configuration information for the first repository is received at the first repository, and repository configuration information for the second repository is received at the second repository. When there is a change defined in the rule set happened in the first repository, a request for data transfer is sent to the clinical data exchange controller, and the clinical data exchange controller then transfers the data to the target repository based on the rule set.

22 Claims, 4 Drawing Sheets

(56) References Cited

U.S. PATENT DOCUMENTS

2019/0243911 A1* 8/2019 Kobozev ................ G16H 30/20
2019/0250998 A1* 8/2019 Bedadala ............ G06F 11/1469
2019/0324652 A1* 10/2019 Vishwakarma ....... G06F 3/0619

* cited by examiner

US 11,232,871 B1

SYSTEM AND METHOD FOR EXCHANGING CLINICAL DATA

BACKGROUND

The subject technology relates generally to clinical data management, and more particularly to exchanging clinical data among parties involved in a clinical trial.

Clinical trials are research studies on participants designed to answer specific questions about biomedical or behavioral interventions, including new treatments (such as drugs and medical devices). A clinical trial may involve a sponsor, a contract research organization ("CRO"), and one or more clinical sites. The sponsor may be a governmental organization, or a pharmaceutical, medical device, or biotechnology company, which defines the clinical trial, initiates the clinical trial, and sends the clinical trial definition to the CRO and the clinical sites. The CRO may receive the clinical trial definition from the sponsor, forward the clinical trial definition to one or more clinical sites, manage clinical sites, receive patient clinical trial source data from the clinical sites and forward the patient clinical trial source data to the sponsor. The clinical sites may receive the clinical trial definition from the sponsor or the CRO, and execute the clinical trial by seeing the patients, capturing patient clinical trial source data, and sending the patient clinical trial source data to the CRO or the sponsor. Traditionally, the sponsor, CRO and clinical sites send each other paper documents to communicate the clinical trial definition, patient clinical trial source data and other information related to the clinical trial. It is desirable to improve efficiency of the process for exchanging clinical data.

SUMMARY

A method for exchanging clinical data in a system comprising a clinical data exchange controller, a first repository and a second repository. The method comprises: receiving first repository configuration information at the first repository, wherein the first repository configuration information comprises a connection to the second repository, a scope of capacity of the first repository, and a rule set of the first repository. The method further comprises: receiving second repository configuration information at the second repository, wherein the second repository configuration information comprises a connection to the first repository, a scope of capacity of the second repository, and a rule set of the second repository. The method further comprises: determining if there is a predetermined change in the first repository based on the first repository configuration information; and copying the predetermined change to the second repository by the clinical data exchange controller when there is the predetermined change in the first repository.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, well-known structures and components are shown in block diagram form in order to avoid obscuring the concepts of the subject technology.

Figure 1:
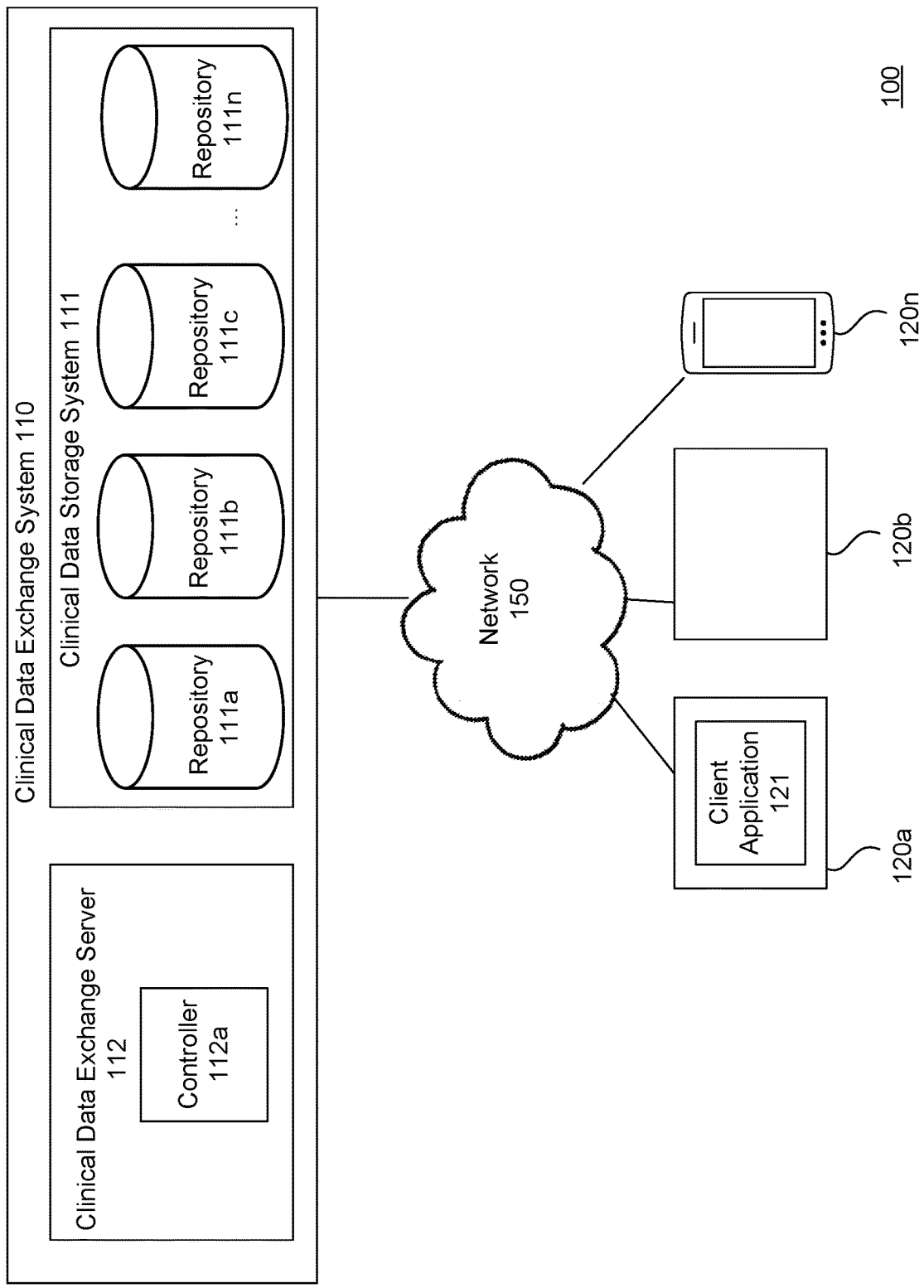
FIG. 1 illustrates an example high level block diagram of an architecture for exchanging clinical data wherein the present invention may be implemented.

FIG. 1 illustrates an example high level block diagram of an architecture 100 for exchanging clinical data wherein the present invention may be implemented. As shown, the architecture 100 may include a clinical data exchange system 110, and a plurality of user computing devices 120a, 120b, ... 120n, coupled to each other via a network 150. The clinical data exchange system 110 may include a clinical data storage system 111 and a clinical data exchange server 112. The clinical data storage system 111 may have a plurality of repositories, e.g., 111a, 111b, 111c, ... and 111n. The network 150 may include one or more types of communication networks, e.g., a local area network ("LAN"), a wide area network ("WAN"), an intra-network, an inter-network (e.g., the Internet), a telecommunication network, and peer-to-peer networks (e.g., ad hoc peer-to-peer networks), which may be wired or wireless.

The user computing devices 120a-120n may be any machine or system that is used by a user to access the clinical data management system 110 via the network 150, and may be any commercially available computing devices including laptop computers, desktop computers, mobile phones, smart phones, tablet computers, netbooks, and personal digital assistants (PDAs). A client application 121 may run from a user computing device, e.g., 120a, and access data in the clinical data exchange system 110 via the network 150.

The clinical data storage system 111 may store clinical data that client applications (e.g., 121) in user computing devices 120a-120n may access and may be any commercially available storage devices. Each content repository (e.g., 111a, 111b, 111c or 111n) may store a specific category of data, and allow users to interact with its data in a specific business context. The repositories may store structured and/or unstructured data. In one implementation, the repository 111a stores data for a sponsor of a clinical trial, the repository 111b stores data for a CRO of the clinical trial, and the repository 111c stores data for a clinical site of the clinical trial. It should be appreciated that content repositories may be separate logic sections in a same storage device.

The clinical data exchange server 112 is typically a remote computer system accessible over a remote or local network, such as the network 150. The clinical data exchange server 112 may store a clinical data exchange controller 112a for controlling management and collection of the clinical data, including the method to be discussed with FIG. 4. The clinical data exchange server 112 could be any commercially available computing devices. Although only one server is shown, it should be appreciated that the clinical data exchange system 110 may have a plurality of servers. A client application (e.g., 121) process may be active on one or more user computing devices 120a-120n. The corresponding server process (e.g., 112a) may be active on the clinical data exchange server 112. The client application process and the corresponding server process may communicate with each other over the network 150, thus providing distributed functionality and allowing multiple client applications to take advantage of the information-gathering capabilities of the clinical data exchange system 110.

In one implementation, the architecture 100 may be used for collecting and managing clinical data, e.g., clinical trial data. A first repository (e.g., 111*a*) may be used by a first sponsor (e.g., a pharmaceutical company) to store definition of a first clinical trial received from a first user computing device (e.g., 120*a*). The definition of the first clinical trial may define the infrastructure and lifecycle of the clinical trial, and may comprise rules (e.g., for queries, derived values, notifications and displaying events, forms and items), a casebook (i.e., a doctor's binder), event groups, events (e.g., patients visits), forms which comprise segregate sections and fields, item groups and items. In one example, the definition may define details of the clinical trial, i.e., each patient may have ten visits, and each visit may have three forms. There may be a workflow associated with each visit, e.g., what needs to be done at each visit.

The sponsor, the CRO and the clinical site need to exchange data and documents related to the first clinical trial to meet regulatory requirements. For example, the sponsor needs to send documents for executing the clinical trial to the CRO, and the CRO distributes such documents to the clinical sites. The site needs to acknowledge that they received the documents, and received forms from the CRO they need to get the patients to fill in. The forms need to be sent back to the CRO. And the CRO has to send all of the completed forms back to the sponsor.

In one implementation, the first clinical trial definition may be stored as definition objects in the first repository 111*a*, specifying what is required to happen on each site during the clinical trial. The first repository 111*a* may also store electronic records of the first clinical trial.

The second repository 111*b* may be used by a CRO of the first clinical trial to store the first clinical trial definition from the sponsor, execution plan of the first clinical trial, and forms for collecting patient data.

The third repository 111*c* may be used by a first clinical site (e.g., a hospital) of the first clinical trial to store clinical trial source data from a second user computing device (e.g., 120*b*). The clinical trial source data (e.g., three blood pressure values of a patient taken during one visit) may be collected on a form and the completed form may be sent to the second repository 111*b*.

The repositories may be configured with user instructions so that they can exchange data and/or documents with each other based on the configuration. The repository configuration information may include connections. The repositories may store configuration information for setting up connections with other repositories, so that a repository is logically connected to one or more target repositories. For example, a sponsor repository (e.g., 111*a*) may be connected to a CRO repository (e.g., 111*b*). A certificate exchange may be used to set up the connection. The certificate may be a public certificate.

The repository configuration information may include scope of capacities. The repositories may store information for defining their relationships and scopes of capacities. In one implementation, the scope of capacity for the repository 111*a* may be, e.g., using the repository 111*b* as your CRO repository for the first clinical trial.

The repository configuration information may include a rule set. The repositories may store the rule set, which defines the data and/or documents to be transferred between two repositories which already have a connection and have their scopes of capacities defined. The rule set may have information such as documents to be transferred, the transfer rules (e.g., direction of the data transfer), and if there is an audit trail. In one example, the rule set may require that all approved resumes are transferred from a clinical site repository (e.g., 111*c*) to a CRO repository (e.g., 111*b*). In one example, the rule set may require that all patient data is transferred from a CRO repository (e.g., 111*b*) to a sponsor repository (e.g., 111*a*). In one example, the rule set may require that an audit trail is transferred from a CRO repository (e.g., 111*b*) to a sponsor repository (e.g., 111*a*).

In one implementation, the connection, scope of capacity and rule set are defined in the repositories. The clinical data exchange server 112 may pull and push the data and/or documents based on the connections, scopes of capacities, and rule sets. When a connection is set up, it is registered with the clinical data exchange server 112. The clinical data exchange server 112 knows that connection, and pulls in data according to the rule sets. In one implementation, the clinical data exchange server 112 may just cache the data, but not persist the data.

In one implementation, after receiving repository configuration information related to connections, scopes of capacities and rule sets, a repository may automatically monitor a predetermined type of changes to a predetermined document and send a request to the clinical data exchange server 112 for updating the target repository with the change when the predetermined type of change happens. The predetermined document, predetermined type of change, and target repository are defined in the rule set, and may be based on regulatory requirements. Industry best practice may be taken into consideration as well. The predetermined type of change may be creating a new document, updating an existing document, or deleting an existing document. In one implementation, when a predetermined document (e.g., definition of a clinical trial) is created in the sponsor repository 111*a*, a request may be sent to the clinical data exchange server 112 for sending a copy of the definition of the clinical trial to the CRO repository 111*b*. When a predetermined document (e.g., definition of a clinical trial) is updated in the sponsor repository 111*a*, a request may be sent to the clinical data exchange server 112 for sending an updated copy of the definition of the clinical trial to the CRO repository 111*b*. When a predetermined document (e.g., definition of a clinical trial) is deleted or expired in the sponsor repository 111*a*, a request may be sent to the clinical data exchange server 112 for deleting the definition of the clinical trial from the CRO repository 111*b*.

With the repositories configured with user instruction and automatically transfer documents to a target repository based on the rule set, users may stay in their repository and wait for documents they need to be sent to their repositories based on the repository confirmation information without having to request the documents and without having to login to different repositories. The documents are transferred not because a user requested it, but because the documents need to be shared based on regulatory requirements.

In one implementation, the repository configuration information may define and enable trial master file ("TMF") transfer between a sponsor and its CRO. The sponsor has asked the CRO to execute the clinical trial, and there are regulatory requirements on both the CRO and the sponsor to have the up-to-date copy of all of the trial master file documents. As the CRO is collecting those documents, as soon as the documents are approved, they appear in the sponsor's repository based on the repository configuration information, before the sponsor requests them.

In one implementation, the repository configuration information may define and enable document transfer between clinical trial sites and a CRO. When a form with new clinical trial source data is saved to the trial site repository 111c, it is automatically transferred to the CRO repository 111b based on the repository configuration information.

The clinical data exchange server 112 may transfer a document to a target repository based on the connections, scope of capacities and rule set. In one implementation, the clinical data exchange server 112 may check for data changes in the repositories, and pull the data and send a copy to the target repository when the data changes meet the criteria in the rule set.

In one implementation, the repositories may determine the data changes and send a request for data transfer to the clinical data exchange server 112 when the data changes meet the criteria in the rule set, instead of using the clinical data exchange server 112 to check for data changes.

In one implementation, a queue may be used to queue data transfer requests from the repositories to the clinical data exchange server 112. When there is a predetermined change in a repository, the repository may determine that it needs to transfer the data to a target repository according to the rule set, and send a transfer request to the queue to trigger the clinical data exchange server 112. The clinical data exchange server 112 may check the queue, check the rule set, and respond to the request by pulling and pushing data when the rule set requires that. In one example, one of the rules might be looking for all approved resumes in the CRO repository 111b. When a resume gets approved in the CRO repository 111b, the repository 111b may send a request to the queue. The clinical data exchange server 112 may check the rule set. When the rule set requires the resume to be shared with the sponsor, the clinical data exchange server 112 may respond by sending a copy of the resume to the sponsor repository 111a accordingly.

If there is new data in the CRO repository 111b, the CRO repository 111b may send a request to the queue. The clinical data exchange server 112 may check the rule set and determine if the sponsor needs it. If yes, it may push the data to the sponsor repository 111a.

From the queued requests, the clinical data exchange server knows pending work for each repository In one implementation, a copy of the new or updated document, instead of a link, is pushed to the target repository in almost real time. Users of the sponsor repository may access the new or updated document in the sponsor repository locally.

The repositories may use different document types. For example, for a same type of document, a sponsor may use "resume" while the CRO may use CV. When transferring a document to a target repository, the clinical data exchange server 112 may map document types to each other. In one implementation, mapping rules may be applied when a same type document is named differently in the repositories. In one implementation, a common model may be used for mapping documents in different repositories. The common model is like a centralized common standard that every repository maps to. Customers of the repositories may define their own documents, but need to map document types in their repositories to those in the common model. For example, the common model may use "CM CV"; the sponsor may use "CV," mapped to "CM CV;" and the CRO may use "resume," also mapped to "CM CV." The document type "CV" and "resume" are essentially the same. The clinical data exchange server 112 may compare the document type from the sponsor repository 111a and that from the CRO repository 111b with the common model, and map the document type from the sponsor repository 111a and that from the CRO repository 111b through "CM CV" in the common model. In one implementation, the rule set may require that everything mapped to CM CV needs to be transferred. In one implementation, a pick list may be provided for the mapping.

Text fields in the repositories may be mapped to each other. In one implementation, metadata may be used for mapping the text fields. In one implementation, a common model may be used for the mapping.

In one implementation, the clinical data exchange system 110 may be a multi-tenant system where various elements of hardware and software may be shared by one or more customers. For instance, a server may simultaneously process requests from a plurality of customers (e.g., sponsors, and clinical sites), and the clinical data storage system 111 may store content for a plurality of customers (e.g., sponsors, and clinical sites). In a multi-tenant system, a user is typically associated with a particular customer. In one example, a user could be an employee of one of a number of pharmaceutical companies, CROs or clinical sites which are tenants, or customers, of the clinical data exchange system 110.

In one embodiment, the clinical data exchange system 110 may run on a cloud computing platform. Users can access content on the cloud independently by using a virtual machine image, or purchasing access to a service maintained by a cloud database provider.

In one embodiment, the clinical data exchange system 110 may be provided as Software as a Service ("SaaS") to allow users to access the clinical data exchange system 110 with a thin client.

Figure 2:
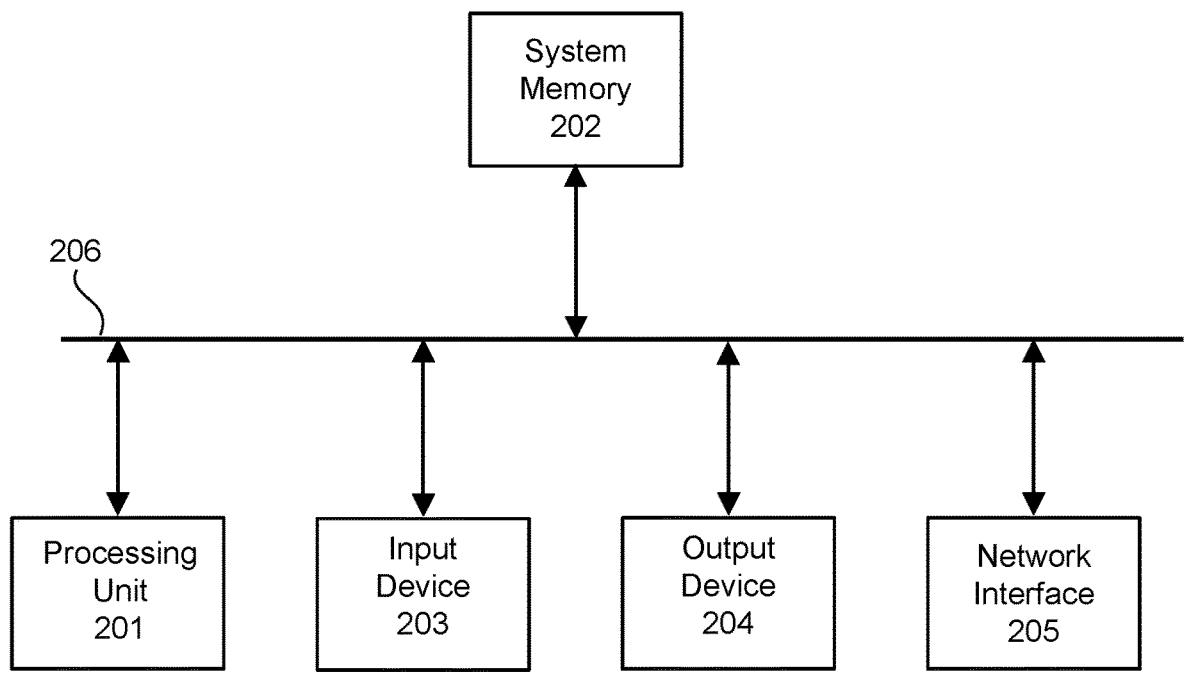
FIG. 2 illustrates an example block diagram of a computing device.

FIG. 2 illustrates an example block diagram of a computing device 200 which can be used as the user computing devices 120a-120n, and the medical data management server 112 in FIG. 1. The computing device 200 is only one example of a suitable computing environment and is not intended to suggest any limitation as to scope of use or functionality. The computing device 200 may include a processing unit 201, a system memory 202, an input device 203, an output device 204, a network interface 205 and a system bus 206 that couples these components to each other.

The processing unit 201 may be configured to execute computer instructions that are stored in a computer-readable medium, for example, the system memory 202. The processing unit 201 may be a central processing unit (CPU).

The system memory 202 typically includes a variety of computer readable media which may be any available media accessible by the processing unit 201. For instance, the system memory 202 may include computer storage media in the form of volatile and/or nonvolatile memory such as read only memory (ROM) and/or random access memory (RAM). By way of example, but not limitation, the system memory 202 may store instructions and data, e.g., an operating system, program modules, various application programs, and program data.

A user can enter commands and information to the computing device 200 through the input device 203. The input device 203 may be, e.g., a keyboard, a touchscreen input device, a touch pad, a mouse, a microphone, and/or a pen.

The computing device 200 may provide its output via the output device 204 which may be, e.g., a monitor or other type of display device, a speaker, or a printer.

The computing device 200, through the network interface 205, may operate in a networked or distributed environment using logical connections to one or more other computing devices, which may be a personal computer, a server, a router, a network PC, a peer device, a smart phone, or any other media consumption or transmission device, and may include any or all of the elements described above. The logical connections may include a network (e.g., the network 150) and/or buses. The network interface 205 may be configured to allow the computing device 200 to transmit and receive data in a network, for example, the network 150. The network interface 205 may include one or more network interface cards (NICs).

Figure 3:
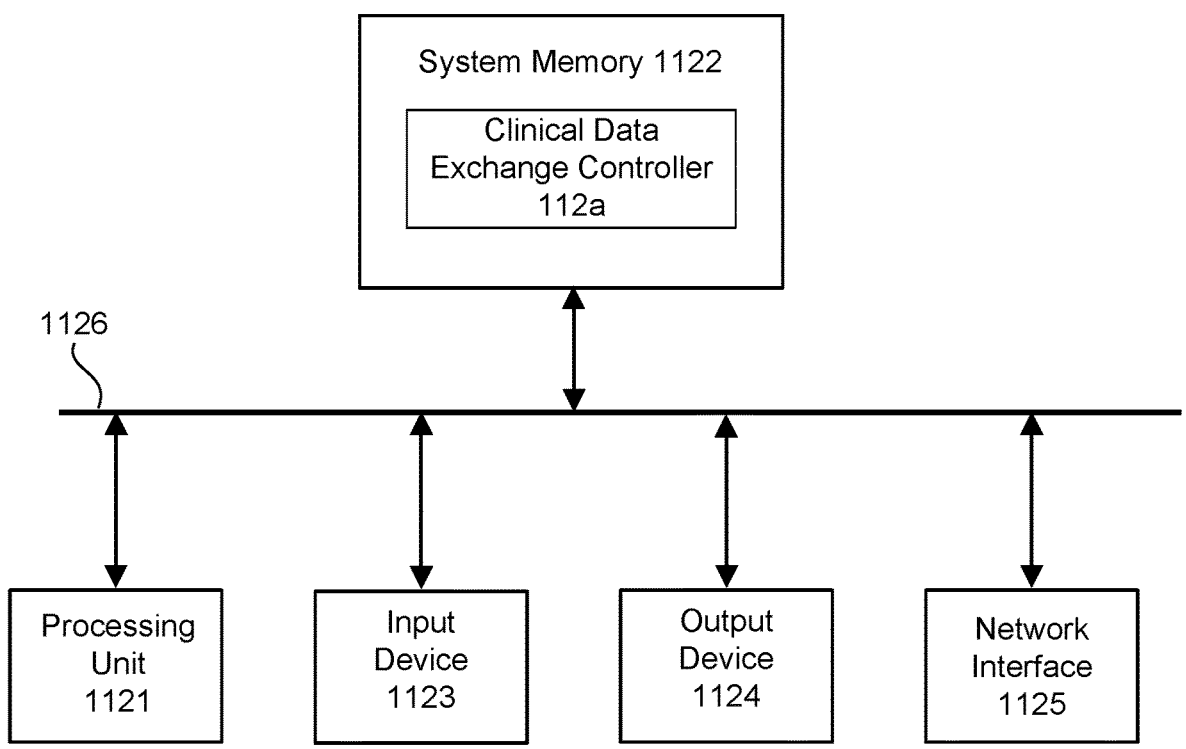
FIG. 3 illustrates an example high level block diagram of the clinical data exchange server according to one embodiment of the present invention.

FIG. 3 illustrates an example high level block diagram of the clinical data exchange server 112 according to one embodiment of the present invention. The medical data management server 112 may be implemented by the computing device 200, and may have a processing unit 1121, a system memory 1122, an input device 1123, an output device 1124, and a network interface 1125, coupled to each other via a system bus 1126. The system memory 1122 may store a clinical data exchange controller 112a.

Figure 4:
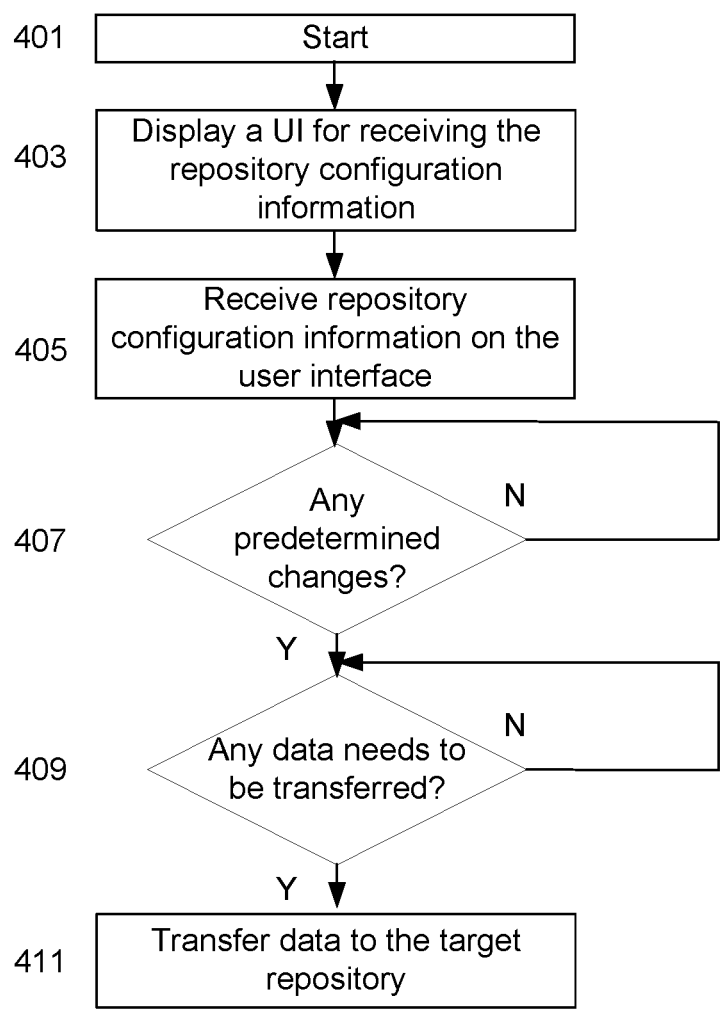
FIG. 4 illustrates an example flowchart of a method for controlling clinical data exchange according to one embodiment of the present invention.

FIG. 4 illustrates an example flowchart of a method for controlling clinical trial data exchange according to one embodiment of the present invention.

The process may start at 401.

At 403, a user interface may be displayed for receiving repository configuration information. The user interface may have a first area for identifying a repository (e.g., the sponsor repository 111a), a second area for receiving connection definition, a third area for receiving the scope of capacities, and a fourth area for receiving rule sets. The connection definition may define a repository's connection to other repositories. The scope of capacities may define the repository's relationships and scopes of capacities. The rule set may define the data and/or documents to be transferred between two repositories which already have a connection and have their scopes of capacities defined.

At 405, configuration information for a first repository (e.g., the sponsor repository 111a) may be received. The configuration information may include connections (e.g., the target repository is the CRO repository 111b), scope of capacities (e.g., use the repository 111b as the CRO repository), and rule sets (e.g., transfer all CVs approved in the CRO repository to the sponsor repository).

At 407, it may be determined if any changed defined in the repository configuration information happened.

In one implementation, the clinical data exchange server 112 may check for data changes in the repositories, and pull the data and send a copy to the target repository when the data changes meet the criteria in the rule set.

In one implementation, repositories may determine the data changes and send a request for data transfer to the clinical data exchange server 112 when the data changes meet the criteria in the rule set.

In one implementation, a queue may be used to queue data transfer requests from the repositories to the clinical data exchange server 112. When there is a predetermined change in a repository, the repository may determine that it needs to transfer the data to a target repository according to the rule set, and send a transfer request to the queue to trigger the clinical data exchange server 112.

At 409, it may be determined, e.g., by the clinical data exchange server 112, if any data or document should be transferred to the target repository according to the rule set.

If yes, the clinical data exchange server 112 may transfer a copy of the data or document to the target repository at 411.

The above-described features and applications can be implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

In this specification, the term "software" is meant to include firmware residing in read-only memory or applications stored in magnetic storage, which can be read into memory for processing by a processor. Also, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs. Examples of computer programs or computer code include machine code, for example is produced by a compiler, and files including higher-level code that are executed by a computer, an electronic component, or a microprocessor using an interpreter.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but is to be accorded the full scope consistent with the language claims, where reference to an element in the singular is not intended to mean "one and only one" unless specifically so stated, but rather "one or more." Unless specifically stated otherwise, the term "some" refers to one or more.

What is claimed is:

1. A computer-implemented method for exchanging clinical data in a computer system comprising a clinical data exchange controller, a first repository and a second repository, the method comprising:
   receiving, by the computer system via a network, first repository configuration information at the first repository, wherein the first repository configuration information comprises a connection to the second repository, a scope of capacity of the first repository, and a rule set of the first repository, wherein the rule set of the first repository defines data to be transferred between the first and second repositories, wherein the scope of capacity of the first repository defines that the first repository stores data for a first party, and wherein the first repository configuration information is received on a first user interface;
   receiving, by the computer system via the network, second repository configuration information at the second repository, wherein the second repository configuration information comprises a connection to the first repository, a scope of capacity of the second repository, and a rule set of the second repository, wherein the rule set of the second repository defines the data to be transferred between the first and second repositories in response to a request, wherein the scope of capacity of the second repository defines that the second repository stores data for a second party, and wherein the second repository configuration information is received on a second user interface, wherein the transferring the data between the first and second repositories includes mapping, via a common model, a first document type in the first repository to a second document type in the second repository, wherein the first user interface is different from the second user interface;
   determining, by the computer system, if there is a predetermined change in the first repository based on the first repository configuration information; and
   copying the predetermined change to the second repository by the clinical data exchange controller when there is the predetermined change in the first repository.

2. The method of claim 1, wherein the first repository determines that there is the predetermined change in the first repository.

3. The method of claim 2, further comprising: sending a request to inform the clinical data exchange controller when there is the predetermined change in the first repository.

4. The method of claim 3, further comprising: queuing the request at a queue for the clinical data exchange controller to respond.

5. The method of claim 1, wherein the data exchange controller determines that there is the predetermined change in the first repository.

6. The method of claim 1, wherein the predetermined change is a new document stored in the first repository.

7. The method of claim 6, further comprising: sending a copy of the new document to the second repository by the clinical data exchange controller.

8. The method of claim 1, wherein the predetermined change is an update to a first document in the first repository.

9. The method of claim 8, further comprising: transferring a copy of the updated first document to the second repository by the clinical date exchange controller.

10. The method of claim 1, wherein the predetermined change is deleting a second document from the first repository.

11. The method of claim 10, further comprising: deleting the second document from the second repository by the clinical data exchange controller.

12. The method of claim 1, wherein the rule set is based on regulatory requirements.

13. The method of claim 1, further comprising: using a public certificate to set up the connection to the second repository.

14. The method of claim 1, wherein the scope of capacity defines how to use the target repository.

15. The method of claim 1, wherein the first repository stores data of a sponsor of a clinical trial.

16. The method of claim 15, wherein the second repository stores data of a contract research organization of the clinical trial.

17. The method of 1, wherein the rule set of the first repository comprises information on documents to be transferred to the second repository.

18. The method of claim 1, further comprising: mapping the first document type to a common model, mapping the second document type to the common model, and mapping the first document type and the second document type through the common model.

19. The method of claim 1, wherein the rule set of the first repository comprises documents to be transferred.

20. The method of claim 1, wherein the rule set of the first repository comprises a transfer rule which defines direction of data transfer.

21. The method of claim 1, wherein the rule set of the first repository defines if there is an audit trail.

22. A system for exchanging clinical data, comprising:
   a processor;
   a first repository, which stores documents for a first party in a clinical trial, receives first repository configuration information via a network, and determines if there is a predetermined change in the first repository based on the first repository configuration information, wherein the first repository configuration information comprises a connection to a second repository, a scope of capacity of the first repository, and a rule set of the first repository, wherein the rule set of the first repository defines data to be transferred between the first and second repositories, the scope of capacity of the first repository defines that the first repository stores data for a first party, and wherein the first repository configuration information is received on a first user interface;

a second repository, which stores documents for a second party in the clinical trial, and receives second repository configuration information via the network, wherein the second repository configuration information comprises a connection to the first repository, a scope of capacity of the second repository, and a rule set of the second repository, wherein the rule set of the second repository defines data to be transferred between the first and second repositories, wherein the scope of capacity of the second repository defines that the second repository stores data for a second party, and wherein the second repository configuration information is received on a second user interface, wherein the first user interface is different from the second user interface;

a clinical data exchange controller in a server in a content management system for copying the predetermined change to the second repository when there is the predetermined change in the first repository, receiving a request for transferring a first document to the second repository, determining if the first document needs to be transferred to the second repository according to the rule set of the first repository, and transferring the first document to the second repository when the rule set of the first repository requires such a transfer, wherein the transferring the first document between the first and second repositories includes mapping, via a common model, a first document type in the first repository to a second document type in the second repository.

* * * * *